United States Patent
Higashiyama (10) Patent No.: US 11,338,100 B2
(45) Date of Patent: May 24, 2022

(54) BLOWING DEVICE AND FLUID CONTROL DEVICE

(71) Applicant: Murata Manufacturing Co., Ltd., Kyoto (JP)

(72) Inventor: Yuzo Higashiyama, Nagaokakyo (JP)

(73) Assignee: MURATA MANUFACTURING CO., LTD., Kyoto (JP)

( * ) Notice: Subject to any disclaimer, the term of this patent is extended or adjusted under 35 U.S.C. 154(b) by 352 days.

(21) Appl. No.: 16/571,649

(22) Filed: Sep. 16, 2019

(65) Prior Publication Data

US 2020/0009337 A1 Jan. 9, 2020

Related U.S. Application Data

(63) Continuation of application No. PCT/JP2019/009415, filed on Mar. 12, 2018.

(30) Foreign Application Priority Data

Mar. 21, 2017 (JP) ............................. JP2017-054808

(51) Int. Cl.
*A61M 16/00* (2006.01)

(52) U.S. Cl.
CPC ..... *A61M 16/0066* (2013.01); *A61M 2205/33* (2013.01)

(58) Field of Classification Search
CPC .. A61M 16/0066; F04D 17/16; F04D 29/083; F04D 29/626; F04D 29/668; A62B 18/006; A42B 3/286
See application file for complete search history.

(56) References Cited

U.S. PATENT DOCUMENTS

| 2009/0162226 A1* | 6/2009 | Campbell | F04D 29/624 |
| | | | 417/423.14 |
| 2011/0277970 A1* | 11/2011 | Tsuji | H05K 7/206 |
| | | | 165/121 |

(Continued)

FOREIGN PATENT DOCUMENTS

| JP | H02-18919 U | 2/1990 |
| JP | 2003-164097 A | 6/2003 |

(Continued)

OTHER PUBLICATIONS

Machine translation of JP-2006038009-A.*

(Continued)

*Primary Examiner* — Joseph D. Boecker
(74) *Attorney, Agent, or Firm* — Pearne & Gordon LLP (57) ABSTRACT

An inner peripheral surface of an upper plate of a first case has a first inclined surface that faces an outer peripheral surface of a seal holding member of a motor in a radial direction of a rotary shaft. An inner peripheral surface of a seal fixing member has a second inclined surface that also faces the outer peripheral surface of the seal holding member in the radial direction. The outer peripheral surface has third and fourth inclined surfaces along an axial direction of the rotary shaft. An outside diameter on sides of the third and fourth inclined surfaces that are far from each other is greater than an outside diameter on sides of the third and fourth inclined surfaces that are near each other. A sealing member is installed in an annular space that is surrounded by the first, second, third, and fourth inclined surfaces.

11 Claims, 6 Drawing Sheets

(56) References Cited

U.S. PATENT DOCUMENTS

| | | | |
|---|---|---|---|
| 2014/0014109 A1* | 1/2014 | Grasmuck | F04D 25/082 |
| | | | 128/204.18 |
| 2015/0176598 A1* | 6/2015 | Haefner | F04D 29/60 |
| | | | 415/55.1 |
| 2017/0211438 A1 | 7/2017 | Suzuki et al. | |
| 2018/0169359 A1 | 6/2018 | Higashiyama et al. | |

FOREIGN PATENT DOCUMENTS

| | | | |
|---|---|---|---|
| JP | 2006-038009 A | | 2/2006 |
| JP | 2006038009 A | * | 2/2006 |
| JP | 2011-106379 A | | 6/2011 |
| JP | 2016-034411 A | | 3/2016 |
| WO | 2017/029950 A1 | | 2/2017 |

OTHER PUBLICATIONS

International Search Report for International Application No. PCT/JP2018/009415, dated Jun. 12, 2018.
Written Opinion for International Application No. PCT/JP2018/009415, dated Jun. 12, 2018.
Japanese Office action for 2019-507554 dated Jul. 14, 2020.

* cited by examiner

BLOWING DEVICE AND FLUID CONTROL DEVICE

CROSS-REFERENCE TO RELATED APPLICATIONS

This non-provisional application is a continuation application of and claims the benefit of International Application No. PCT/JP2018/009415, which is filed on Mar. 12, 2018 and based upon and claims the benefit of priority from prior Japanese Patent Application No. 2017-054808 filed on Mar. 21, 2017. The contents of the prior applications are incorporated herein by reference in their entireties.

TECHNICAL FIELD

The present disclosure relates to a blowing device that is used in a continuous positive airway pressure (CPAP) device or the like, and more specifically, to a fluid control device including the blowing device.

BACKGROUND

A fluid control device such as a continuous positive airway pressure (CPAP) device (hereafter, CPAP device) is used in the prior art for treatment of sleep-related disorders such as obstructive sleep apnea (OSA) (for example, refer to Patent Document 1: Japanese Laid-Open Patent Publication No. 2016-34411). The CPAP device includes a blowing device that incorporates a fan and supplies a gas (e.g. air) at a pressure higher than atmospheric pressure from the blowing device to a mask attached to the mouth or nose of a patient. The CPAP device is used when the patient is sleeping.

BRIEF SUMMARY

The blowing device used in a CPAP device has a motor that vibrates and produces noise thereby adversely affecting the quietness. Accordingly, it is an objective of the present disclosure to reduce the noise produced by vibration of the motor.

A blowing device that solves the above problem includes a fan, a motor, a fan case, and an elastic and annular sealing member. The motor includes a rotation shaft to which the fan is coupled. The fan case accommodates the fan and includes a motor insertion port into which the motor is inserted. The sealing member is located between the motor insertion port and the motor. The fan case includes the motor insertion port into which the motor is inserted, an inlet for drawing gas into the fan case as the fan rotates, and a discharge portion configured to discharge gas out of the fan case as the fan rotates. An inner circumferential surface of the motor insertion port includes a first inclined surface and a second inclined surface that is located at an axially-outer region of the fan case than the first inclined surface. The first inclined surface and the second inclined surface each have an inner diameter that is smaller at a side farther from the other surface than a side closer to the other surface. The motor includes an outer circumferential surface opposed to the inner circumferential surface of the motor insertion port. The outer circumferential surface of the motor includes a third inclined surface and a fourth inclined surface that is located toward an axially-outer side of the fan case than the third inclined surface. The third inclined surface and the fourth inclined surface each have an outer diameter that is larger at a side farther from the other surface than a side closer to the other surface. The sealing member contacts at least one of the first inclined surface and the second inclined surface and at least one of the third inclined surface and the fourth inclined surface.

The inclined surface in this specification includes a surface that extends linearly relative to an axial direction of the rotation shaft of the motor in a cross-section taken in a radial direction about the rotation shaft of the motor. That is, the inclined surface in this specification includes a tapered surface, of which the inner diameter or the outer diameter gradually increases or decreases, and a surface that is curved in an arcuate manner.

With this configuration, the vibration of the motor along the rotation shaft is transmitted from the third inclined surface or the fourth inclined surface through the sealing member to the second inclined surface or the first inclined surface of the fan case. The first inclined surface and the fourth inclined surface or the second inclined surface and the third inclined surface act so that the vibration of the motor along the rotation shaft form an element corresponding to the inclination at a location where each of the inclined surfaces contacts the sealing member. This reduces the vibration of the fan case and the noise resulting from the vibration of the motor.

In the above blowing device, the motor preferably includes a motor body, which drives the fan, and a motor-side fastener, which includes the outer circumferential surface and to which the motor body is fixed. With this configuration, the third inclined surface and the fourth inclined surface can easily be set relative to the motor body including the rotation shaft.

In the above blowing device, the motor-side fastener preferably includes a first fastener, which includes the third inclined surface, and a second fastener, which includes the fourth inclined surface. With this configuration, the third inclined surface and the four inclined surface can easily be set relative to the motor body including the rotation shaft.

The blowing device preferably includes a viscous member located between the first fastener and the second fastener. With this configuration, the viscous member reduces the vibration of the fan case.

In the above blowing device, the fan case preferably includes a case body and a case-side fastener. The case body defines an accommodation space for accommodating the fan. The case-side fastener is coupled to an upper surface of the case body. The case body includes the first inclined surface, and the case-side fastener includes the second inclined surface. This configuration facilitates the assembly of the fan case and improves productivity.

In the above blowing device, the fan case preferably includes a case body and a case-side fastener. The case body defines an accommodation space for accommodating the fan. The case-side fastener is coupled to an upper surface of the case body. The case-side fastener includes the first inclined surface and the second inclined surface. This configuration facilitates the assembly of the fan case and improves productivity.

In the above blowing device, the case body and the case-side fastener are preferably formed from different materials. This configuration further reduces vibration and noise of the fan case.

The above blowing device preferably includes a viscous member located between the case body and the case-side fastener. With this configuration, the viscous member reduces vibration of the fan case.

In the above blowing device, the viscous member preferably includes an adhesive sheet or a gel sheet.

In the above blowing device, it is preferred that at least one of the first inclined surface and the second inclined surface are curved to be concave radially outward, and at least one of the third inclined surface and the fourth inclined surface is curved to be concave radially outward.

A fluid control device that solves the above problem includes the above-described blowing device and a controller that controls the blowing device. This configuration reduces vibration of the fan case and noise produced by vibration of the motor.

The blowing device and fluid control device in accordance with the present disclosure reduce noise produced by vibration of the motor.

DETAILED DESCRIPTION

One embodiment will now be described. The drawings may not be to scale, and the relative size, proportions, and depiction of elements in the drawings may be exaggerated for clarity, illustration, and convenience. Moreover, to facilitate understanding, hatching lines may not be illustrated in the cross-sectional drawings.

Figure 1:
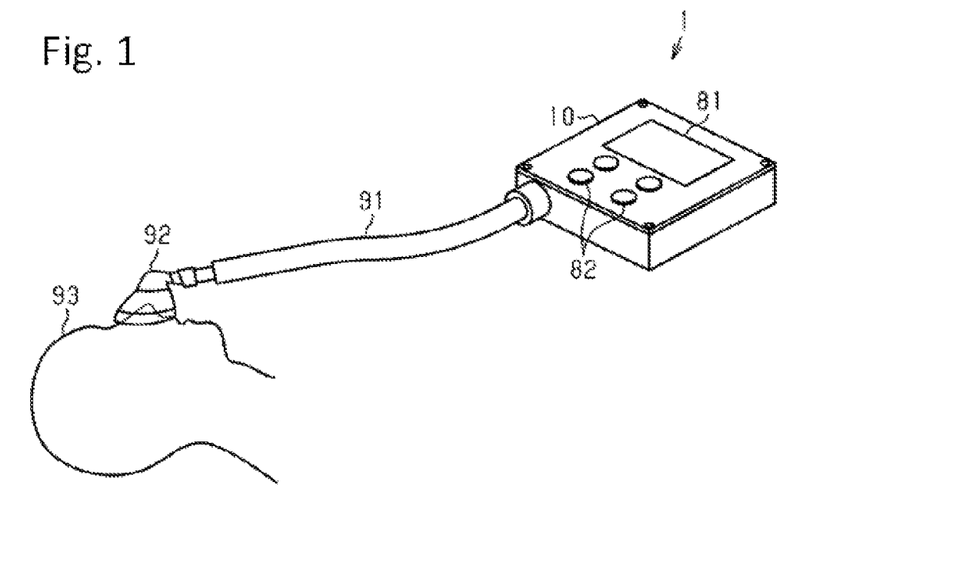
FIG. 1 is a schematic diagram of a fluid control device.

As shown in FIG. 1, a fluid control device 1 is used, for example, as a continuous positive airway pressure (CPAP) device. The fluid control device 1 is connected to a mask 92 by a tube 91. The mask 92 is attached to the nose or mouth of a patient 93. The fluid control device 1 supplies a gas (e.g., air) at a desired pressure via the tube 91 and the mask 92 to the patient 93. Further, the fluid control device 1 determines a state (e.g., exhaling) of the patient 93 and controls the pressure of the gas supplied to the patient 93 in accordance with the state of the patient.

The fluid control device 1 includes a case 10, a display 81, and an operation portion 82. The display 81 and the operation portion 82 are located on an upper surface of the case 10. The fluid control device 1 displays various types of information including setting values on the display 81. Further, the fluid control device 1 sets various types of information including the setting values based on an operation of the operation portion 82. The setting values include a pressure value of the supplied gas and a flow rate value of the gas. Also, the setting values include a pressure value of the gas supplied when exhaling.

For example, the fluid control device 1 estimates an exhalation state of the patient 93 wearing the mask 92. Then, the fluid control device 1 controls the pressure value of the supplied gas in accordance with the estimated exhalation state. For example, the pressure when inhaling is 1000 [Pa], and the pressure when exhaling is 700 [Pa]. When the patient 93 is exhaling, the fluid control device 1 decreases the pressure of the supplied gas to alleviate difficulty in breathing by the patient 93.

Figure 2A:
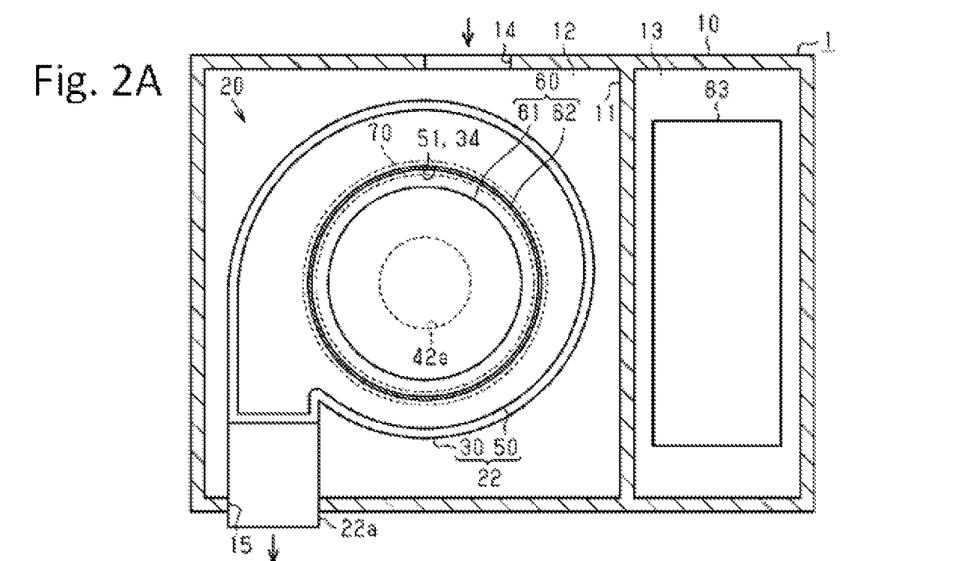
FIG. 2A is a schematic cross-sectional plan diagram of the fluid control device.
Figure 2B:
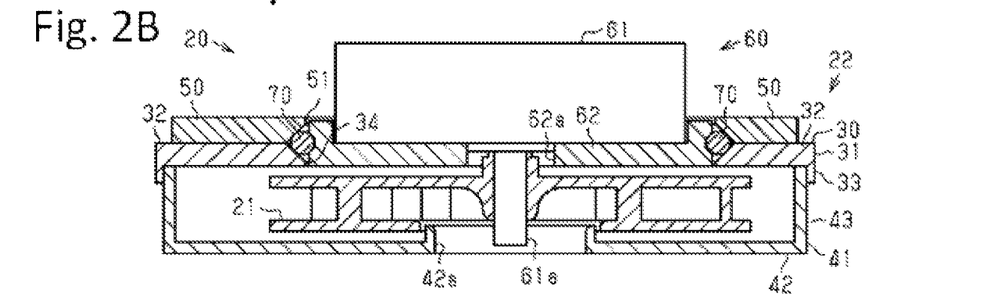
FIG. 2B is a schematic cross-sectional side diagram of the fluid control device.

As shown in FIGS. 2A and 2B, the fluid control device 1 includes the case 10, a blowing unit 20 serving as a blowing device, and a control unit 83. The case 10 includes a partition wall 11 that partitions the interior space. One side of the interior space partitioned by the partition wall 11 is a blowing chamber 12, and the other side of the interior space is a control chamber 13. The blowing unit 20 is arranged in the blowing chamber 12, and the control unit 83 is arranged in the control chamber 13. The control unit 83 serves as a controller that controls the blowing unit 20.

The case 10 includes an inlet 14 that connects the inside and outside of the blowing chamber 12. The inlet 14 is arranged to draw gas from outside of the case 10 into the blowing chamber 12. Further, the case 10 includes an insertion port 15 through which the blowing unit 20 is inserted.

As shown in FIG. 2B, the blowing unit 20 includes a fan 21, a fan case 22, and a motor 60. The fan case 22 accommodates the fan 21. The motor 60 is a drive source, which rotates and drives the fan 21.

Figure 4:
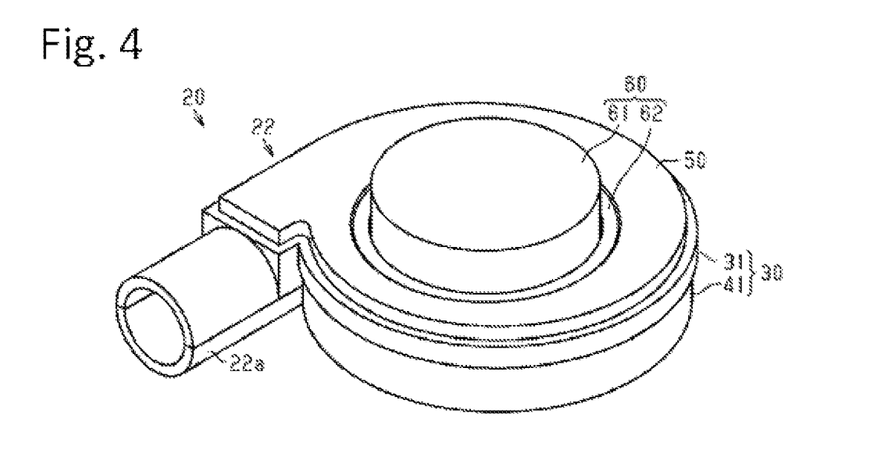
FIG. 4 is a schematic perspective view of the blowing device.

As shown in FIGS. 2B and 4, the fan case 22 includes a case body 30 and a seal fastener 50 fixed to the case body 30. The case body 30 accommodates the fan 21, and includes a first case 31 and a second case 41. The first case 31 includes an upper wall 32 and a side wall 33. The side wall 33 is frame-shaped and extends from an end portion of the upper wall 32 in a direction orthogonal to the upper wall 32.

The second case 41 includes a bottom wall 42 and a side wall 43. The side wall 43 is frame-shaped and extends from an end portion of the bottom wall 42 in the direction orthogonal to the bottom wall 42. The bottom wall 42 includes an inlet 42a that opens downward. The fan case 22 includes a discharge portion 22a that projects from the side surface of the fan case 22 in a state in which the first case 31 is coupled to the second case 41. The discharge portion 22a discharges gas out of the fan case 22. As shown in FIG. 2A, the discharge portion 22a is inserted through the insertion port 15 of the case 10. A distal end of the discharge portion 22a extends through the insertion port 15 and projects out of the case 10. The projected distal end of the discharge portion 22a is connected to the tube 91 shown in FIG. 1.

As shown in FIG. 2B, the upper wall 32 of the first case 31 includes an insertion opening 34 into which the motor 60 is inserted. The seal fastener 50 is fixed to an upper surface of the upper wall 32. The seal fastener 50 is fixed to the upper wall 32 of the first case 31 (e.g., by screws). The seal fastener 50 includes an insertion opening 51 into which the motor 60 is inserted. The material of the first case 31 and the second case 41 may be resin such as acrylic resin. The material of the seal fastener 50 may be a material having a mass larger than that of the first case 31 and the second case 41 (e.g., a metal such as stainless steel).

The motor 60 includes a motor body 61 and a seal holding member 62. The motor body 61 includes a rotation shaft 61*a* defining a radial direction and axial direction, and the seal holding member 62 supports the motor body 61 on the fan case 22. The seal holding member 62 is substantially disc-shaped and includes an insertion hole 62*a*. The rotation shaft 61*a* is inserted through the center of the insertion hole 62*a*. The outer diameter of the seal holding member 62 is set to be smaller than the inner diameter of the insertion opening 34 of the first case 31 and the insertion opening 51 of the seal fastener 50.

The dimension of the motor body 61 in an axial direction of the rotation shaft 61*a* is smaller than the dimension of the motor body 61 in a radial direction of the rotation shaft 61*a*, so as to form a flat motor or a substantially disc-shaped motor. The motor body 61 includes a substantially disc-shaped rotor, and the rotation shaft 61*a* is fixed at the center of the rotor so as to be rotated integrally with the rotor. The rotor is located to oppose a stator in the axial direction of the rotation shaft 61*a*. The fan 21 is fixed to the rotation shaft 61*a*. The motor body 61 is supplied with power to rotate the rotation shaft 61*a* so that the rotation shaft 61*a* rotates integrally with the fan 21.

A sealing member 70 is located between the seal holding member 62 of the motor 60, the first case 31, and the seal fastener 50. The sealing member 70 couples the motor 60 to the case body 30 (first case 31 and seal fastener 50). The sealing member 70 is elastic and annular. The material of the sealing member 70 may be rubber. The sealing member 70 is, for example, an O-ring.

Figure 2C:
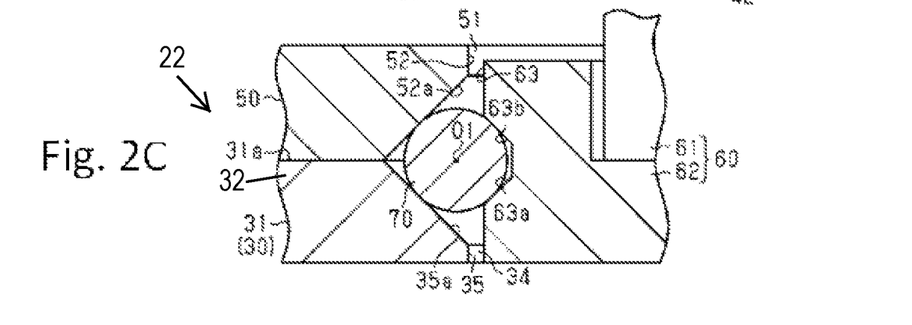
FIG. 2C is a partially enlarged cross-sectional diagram of a blowing device.

The case body 30 and seal fastener 50 define a receptacle (34 and 51) into which the motor 60 is inserted. More specifically, as shown in FIG. 2C, the upper wall 32 of the first case 31 includes an inner circumferential surface 35. The inner circumferential surface 35 includes a first inclined surface 35*a* opposed to the seal holding member 62 of the motor 60 in the radial direction of the rotation shaft 61*a*. Meanwhile, the seal fastener 50 includes an inner circumferential surface 52 having a second inclined surface 52*a* opposed to the seal holding member 62 of the motor 60 in the radial direction. The first inclined surface 35*a* and second inclined surface 52*a* are arranged in the axial direction of the rotation shaft 61*a* such that the second inclined surface 52*a* is located at an axially-outer region of the fan case 22 than the first inclined surface 35*a*.

The first inclined surface 35*a* has an inner diameter that is larger at a side of the first inclined surface 35*a* closer to the second inclined surface 52*a* than aside of the first inclined surface 35*a* farther from the second inclined surface 52*a*. The second inclined surface 52*a* has an inner diameter that is larger at a side of the second inclined surface 52*a* closer to the first inclined surface 35*a* than a side of the second inclined surface 52*a* farther from the first inclined surface 35*a*. That is, the first inclined surface 35*a* and the second inclined surface 52*a* each have an inner diameter that is smaller at the side farther from the other surface than the side closer to the other surface.

In the present embodiment, the first inclined surface 35*a* is tapered in an inside-outside axial direction of the case 10 (bottom-top direction in FIG. 2C) so that the inner diameter of the first inclined surface 35*a* gradually decreases toward the inner side of the case 10. The second inclined surface 52*a* is tapered in the inside-outside axial direction of the case 10 so that the inner diameter of the second inclined surface 52*a* gradually decreases toward the outer side of the case 10.

The seal holding member 62 of the motor 60 includes an outer circumferential surface 63 opposed to the inner circumferential surface of the fan case 22 (inner circumferential surface 35 of case body 30 (first case 31) and inner circumferential surface 52 of seal fastener 50). The outer circumferential surface 63 includes a third inclined surface 63*a* and a fourth inclined surface 63*b* arranged in the axial direction of the rotation shaft 61*a* such that the fourth inclined surface 63*b* is located at an axially-outer region of the fan case 22 than the third inclined surface 63*a*. The third inclined surface 63*a* has an inner diameter that is larger at a side of the third inclined surface 63*a* closer to the fourth inclined surface 63*b* than a side of the third inclined surface 63*a* farther from the fourth inclined surface 63*b*. The fourth inclined surface 63*b* has an inner diameter that is larger at a side of the fourth inclined surface 63*b* closer to the third inclined surface 63*a* than a side of the fourth inclined surface 63*b* farther from the third inclined surface 63*a*. That is, the third inclined surface 63*a* and the fourth inclined surface 63*b* each have an outer diameter that is larger at the side farther from the other surface than the side closer to the other surface.

In the present embodiment, the third inclined surface 63*a* is tapered so that the outer diameter of the third inclined surface 63*a* gradually increases toward the distal end of the rotation shaft 61*a* (downward in FIG. 2C). The fourth inclined surface 63*b* is tapered so that the outer diameter of the fourth inclined surface 63*b* gradually increases in a direction extending away from the distal end of the rotation shaft 61*a* (upward in FIG. 2C).

As shown in FIG. 2C, the sealing member 70 is located in an annular space surrounded by the first inclined surface 35*a*, the second inclined surface 52*a*, the third inclined surface 63*a*, and the fourth inclined surface 63*b*. As shown in FIG. 2A, a gap is provided between the receptacles 51 and 34 of the fan case 22 and the seal holding member 62 of the motor 60 (and extends from the receptacles 51 and 34 to the sealing holding member 62) so that part of the sealing member 70 can be checked through the gap. The outer diameter of the sealing member 70 is larger than the inner diameter of the insertion openings 51 and 34, and the inner diameter of the sealing member 70 is smaller than the outer diameter of the seal holding member 62 of the motor 60.

The fan case 22 and the seal holding member 62 of the motor 60 are set so that the pressure applied to the sealing member 70 will be 0 (zero) or a negative value. The pressure applied to the sealing member 70 indicates the force that elastically deforms the sealing member 70. The annular sealing member 70 has a circular cross section taken along a plane orthogonal to a circumferential direction of the sealing member 70. When the distance from center O1 of the sealing member 70 to each of the first inclined surface 35*a*, the second inclined surface 52*a*, the third inclined surface 63*a*, and the fourth inclined surface 63*b* is equal to or slightly greater than the radius of the cross section of the sealing member 70, pressure will not be applied to the sealing member 70.

The first inclined surface 35*a*, the second inclined surface 52*a*, the third inclined surface 63*a*, and the fourth inclined surface 63*b* are distanced apart so that pressure will not be applied to the sealing member 70 and so that the sealing member 70 is held in a space substantially defined by the first inclined surface 35*a*, the second inclined surface 52*a*, the third inclined surface 63*a*, and the fourth inclined surface 63*b*. In this manner, the motor 60 is supported by the sealing member 70 on the fan case 22.

Operation

The operation of the fluid control device 1 will now be described. As shown in FIG. 2B, the blowing unit 20 includes the fan 21, the fan case 22 that accommodates the fan 21, the motor 60 that drives the fan 21, and the sealing member 70 located between the fan case 22 and the motor 60. The motor 60 is supported by the sealing member 70 on the fan case 22. The fan case 22 and the seal holding member 62 of the motor 60 are set so that the pressure applied to the sealing member 70 will be 0 (zero) or a negative value.

When the motor 60 rotates and drives the fan 21, the rotation of the fan 21 draws gas from the outside of the fan case 22 through the inlet 42a and into the inside of the fan case 22. The gas inside the fan case 22 is discharged through the discharge portion 22a shown in FIG. 2A. The discharged gas is delivered through the tube 91 and the mask 92, which are shown in FIG. 1, to the patient 93.

In this case, the pressure inside the fan case 22 pushes the motor 60 upward. The movement of the motor 60 presses the third inclined surface 63a of the seal holding member 62, which is shown in FIG. 2C, against the sealing member 70. Accordingly, the sealing member 70 comes into intimate contact with the third inclined surface 63a of the seal holding member 62 and the second inclined surface 52a of the seal fastener 50. Thus, in the blowing unit 20, the sealing performance of the sealing member 70 prevents the leakage of gas from a portion other than the discharge portion 22a (refer to FIG. 2A).

As described above, the pressure applied to the sealing member 70 is set to 0 (zero) or a negative value. As long as a gap is slight between the sealing member 70 and the first inclined surface 35a, the second inclined surface 52a, the third inclined surface 63a, and the fourth inclined surface 63b, a sealing will be ensured when the pressure produced inside the fan case 22 presses the motor 60 outward from the fan case 22.

The blowing unit 20 includes a substantially disc-shaped motor body 61. The motor body 61 includes the rotor and the stator opposed toward each other in the axial direction of the rotation shaft 61a. In the motor body 61, vibration is generated in the direction orthogonal to the axial direction of the rotation shaft 61a and in the axial direction of the rotation shaft 61a.

In the blowing unit 20, the vibration in the direction orthogonal to the rotation shaft 61a generated when the motor 60 is driven can be reduced by balancing the motor body 61 and the fan 21.

More specifically, in a blowing unit in which a motor is fixed to an upper surface of a ceiling wall of a fan case, the vibration of the motor generated in an axial direction of a rotation shaft will be directly transmitted to the fan case. Thus, in the fan case, the wall (ceiling wall), to which the motor is fixed, will be greatly vibrated in a direction perpendicular to the upper surface. The vibration noise will be released from the case as noise to the user.

Meanwhile, in the blowing unit 20 of the present embodiment, the motor 60 is supported by the sealing member 70 on the fan case 22. The fan case 22 includes the first inclined surface 35a of the first case 31 and the second inclined surface 52a of the seal fastener 50. The seal holding member 62 of the motor 60 includes the third inclined surface 63a and the fourth inclined surface 63b.

Figure 3A:
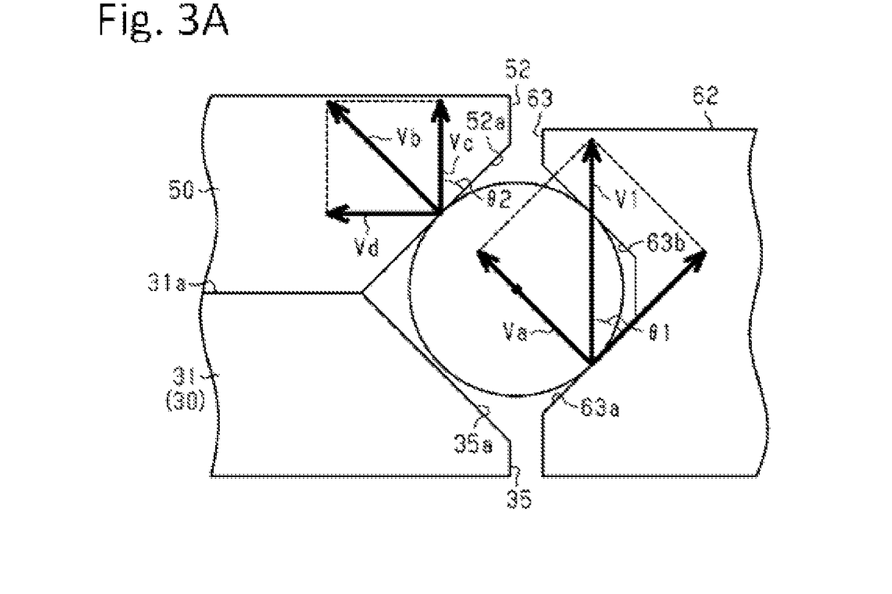
FIG. 3A and FIG. 3B are schematic diagrams of the blowing device.

As shown in FIG. 3A, actuation of the motor 60 will move the motor 60 upward as viewed in the drawing. The sealing member 70 will contact the second inclined surface 52a of the fan case 22 and the third inclined surface 63a of the motor 60. Thus, the vibration of the motor 60 will be transmitted from the third inclined surface 63a of the seal holding member 62 to the sealing member 70 and then to the fan case 22.

In this case, force V1 acting in the axial direction of the rotation shaft 61a (top-bottom direction in FIG. 3A) has an element Va acting in the direction orthogonal to the third inclined surface 63a with respect to the sealing member 70 contacting the third inclined surface 63a. In the same manner, force V1 has an element Vb acting in the direction orthogonal to the second inclined surface 52a with respect to the second inclined surface 52a contacting the sealing member 70. Element Vb includes an element Vc acting in a direction orthogonal to a main surface of the fan case 22 and an element Vd acting in a direction parallel to the main surface of the fan case 22. Element Vc acting in the direction orthogonal to the main surface of the fan case 22 corresponds to the force that vibrates the main surface of the fan case 22, namely, the upper wall 32 of the first case 31.

The magnitude of element Vc is in accordance with angle θ1 of the third inclined surface 63a contacting the sealing member 70, angle θ2 of the second inclined surface 52a contacting the sealing member 70, and the elastic force of the sealing member 70.

First, a case that does not take into consideration the elastic force of the sealing member 70 will now be described.

Vibration element V1 applied to the sealing member 70 is expressed as below.

$Va = V1 \times \sin θ1$ $Vb = Va \times \sin(90° - θ1 + θ2)$ $Vc = Vb \times \sin θ2$ Therefore, in the fan case 22, force (element) Vc acting in the direction perpendicular to an upper surface 31a of the first case 31 is expressed as shown below.

$Vc = V1 \times \sin θ1 \sin θ2 (\sin θ2 \sin θ1 + \cos θ2 \cos θ1)$

Element Vc decreases as angle θ1 of the third inclined surface and angle θ2 of the second inclined surface decrease. This decreases force Vc that vibrates the fan case 22.

Taking into consideration the elastic force of the sealing member 70, element Vb applied from the sealing member 70 to the second inclined surface 52a is decreased from the value obtained from above equation in accordance with the elastic force of the sealing member 70. That is, the elastic force of the sealing member 70 decreases force Vc that vibrates the fan case 22 from the value obtained from above equation.

As angle θ1 of the third inclined surface 63a and angle θ2 of the second inclined surface 52a decrease from ninety degrees, more force that vibrates the fan case 22 will be transmitted by the third inclined surface 63a, the sealing member 70, and the second inclined surface 52a to the fan case 22 thereby decreasing the force that vibrates the fan case 22.

When the motor 60 is moved downward, the same applies as when the motor 60 is moved upward in FIG. 3A. That is, when the motor 60 vibrates in the top-bottom direction, that is, in the axial direction of the rotation shaft 61a as shown in FIG. 2B, the vibrating force will be decreased in accordance with above-described equation and the elastic force of the sealing member 70 and then transmitted to the fan case 22. This reduces the vibration of the fan case 22.

Figure 3B:
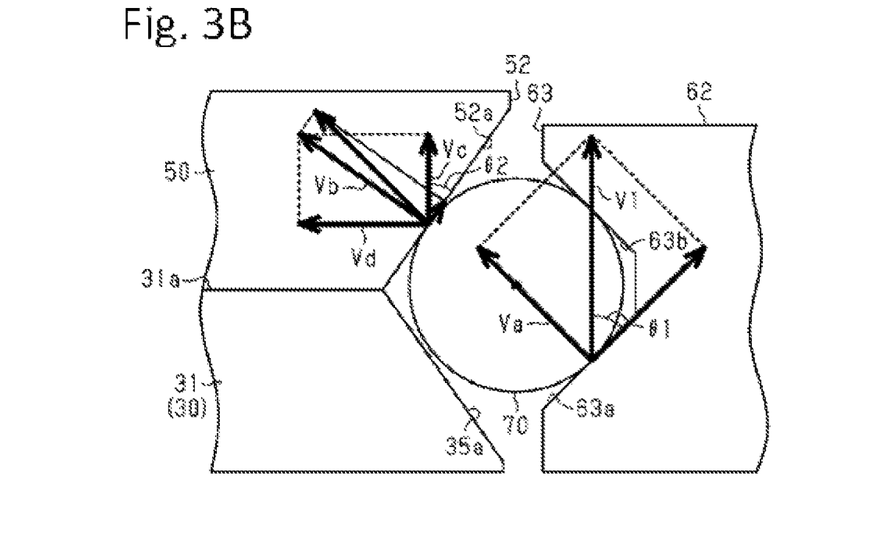

FIG. 3B shows elements V1 to Vd when angle θ1 of the third inclined surface 63a differs from angle θ2 of the second inclined surface 52a (θ2<θ1). When angle θ2 of the second inclined surface 52a is smaller than angle θ1 of the third inclined surface 63a, element Vc will be smaller compared to when angle θ2 of the second inclined surface 52a is equal to angle θ1 of the third inclined surface 63a. This further reduces the force that vibrates the fan case 22.

Further, in the present embodiment, the size of the seal holding member 62 and the fan case 22 is set so that pressure will not be applied to the sealing member 70. Accordingly, compared to when pressure is applied to the sealing member 70, the vibrating force of the motor 60 will be further decreased by the elastic deformation of the sealing member 70 when transmitted to the fan case 22. This further reduces the vibration of the fan case 22. Thus, the sound (noise) resulting from the vibration of the fan case 22 will be further reduced.

In the present embodiment, the fan case 22 includes the first case 31, the second case 41, and the seal fastener 50 that is fixed to the first case 31. The first case 31 and the second case 41 are made of resin and the seal fastener 50 is made of a metal. Thus, the seal fastener 50 that has a mass greater than that of the first case 31 prevents the vibration of the fan case 22 resulting from the transmitted force.

As described above, the present embodiment has the following advantages.

(1) The inner circumferential surface 35 of the upper wall 32 of the first case 31 includes the first inclined surface 35a opposed to the seal holding member 62 of the motor 60 in the radial direction. The inner circumferential surface 52 of the seal fastener 50 includes the second inclined surface 52a opposed to the seal holding member 62 of the motor 60 in the radial direction. The seal holding member 62 of the motor 60 includes the outer circumferential surface 63 opposed to the inner circumferential surface of the fan case 22 (inner circumferential surface 35 of case body 30 (first case 31) and inner circumferential surface 52 of seal fastener 50). The outer circumferential surface 63 includes the third inclined surface 63a and the fourth inclined surface 63b arranged in the axial direction of the rotation shaft 61a. The third inclined surface 63a and the fourth inclined surface 63b each has an outer diameter that is larger at the side farther from the other surface than the side closer to the other surface. The sealing member 70 is located in the annular space surrounded by the first inclined surface 35a, the second inclined surface 52a, the third inclined surface 63a, and the fourth inclined surface 63b.

With this configuration, the vibration of the motor body 61 along the rotation shaft 61a is transmitted from the third inclined surface 63a or the fourth inclined surface 63b through the sealing member 70 to the second inclined surface 52a or the first inclined surface 35a of the fan case 22. The first inclined surface 35a and the fourth inclined surface 63b, or the second inclined surface 52a and the third inclined surface 63a act so that the vibration of the motor body 61 along the rotation shaft 61a forms an element corresponding to the inclination at a location where each of the inclined surfaces 35a, 52a, 63a, and 63b contacts the sealing member 70. This reduces the vibration of the fan case 22 and the noise resulting from the vibration of the motor body 61.

(2) The motor 60 includes the motor body 61 and the seal holding member 62 fixed to the motor body 61. The seal holding member 62 includes the third inclined surface 63a and the fourth inclined surface 63b on the outer circumferential surface 63. With this configuration, the third inclined surface 63a and the fourth inclined surface 63b can easily be set in the motor body 61.

(3) The fan case 22 includes the case body 30, which accommodates the fan 21, and the seal fastener 50, which is coupled to the case body 30. The case body 30 includes the first inclined surface 35a, and the seal fastener 50 includes the second inclined surface 52a. This facilitates the assembly of the fan case 22 and improves productivity.

Modified Examples

The above embodiment may be modified as follows. Reference numerals of components that will not be described may be omitted from the following modified examples.

Figure 5:
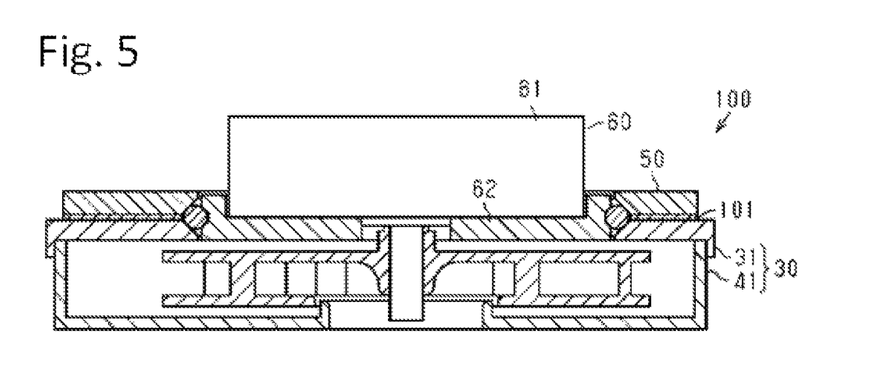
FIG. 5 is a schematic cross-sectional diagram showing a modified example of the blowing device.

The configuration of the blowing unit 20 may be changed. For example, as shown in FIG. 5, a fan case 100 may include a viscous member 101 located between the first case 31 and the seal fastener 50. The viscous member 101 may be an adhesive sheet or a gel sheet. Such a viscous member 101 reduces the vibration of the fan case 100.

Figure 6:
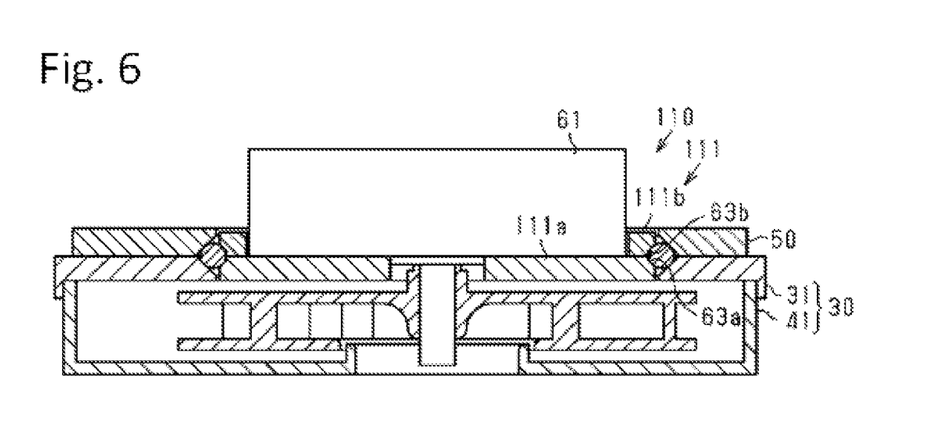
FIG. 6 is a schematic cross-sectional diagram showing another modified example of the blowing device.

As shown in FIG. 6, a seal holding member 111 of a motor 110 includes a first holding member 111a and a second holding member 111b. The first holding member 111a includes the third inclined surface 63a. The second holding member 111b is fixed to the first holding member 111a and includes the fourth inclined surface 63b. Such a seal holding member 111 facilitates machining of the third inclined surface 63a and the fourth inclined surface 63b.

Figure 7:
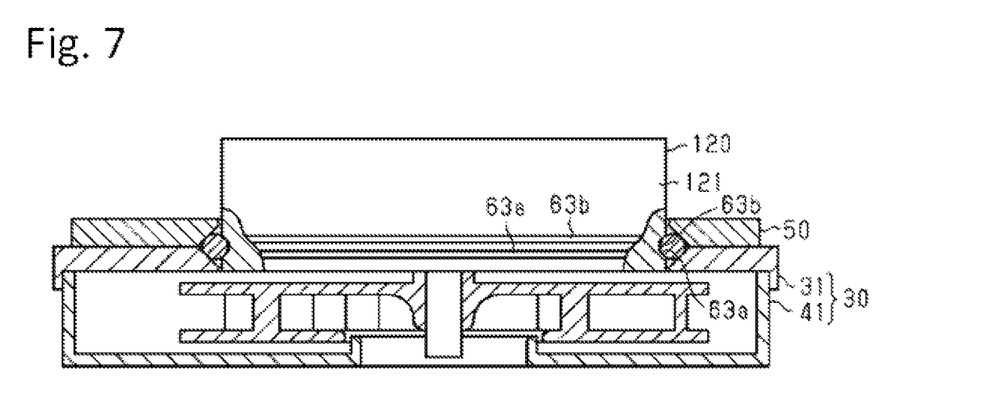
FIG. 7 is a schematic cross-sectional diagram showing yet another modified example of the blowing device.

As shown in FIG. 7, a motor 120 includes the third inclined surface 63a and the fourth inclined surface 63b in a side surface of a motor body 121.

Figure 8A:
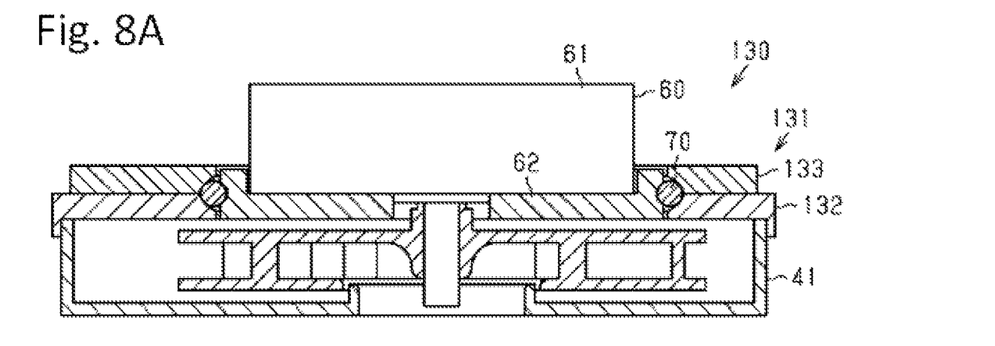
FIG. 8A is a schematic cross-sectional diagram showing still yet another modified example of the blowing device.
Figure 8B:
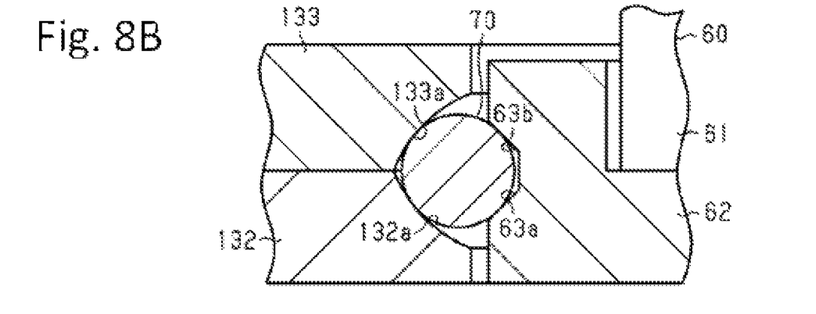
FIG. 8B is a partially enlarged cross-sectional diagram of FIG. 8A.

A blowing unit device 130 shown in FIG. 8A includes a fan case 131, the motor 60, and the sealing member 70. The fan case 131 includes a first case 132, the second case 41, and a seal fastener 133. As shown in FIG. 8B, the first case 132 includes a first inclined surface 132a, and the seal fastener 133 includes a second inclined surface 133a. The first inclined surface 132a is a curved surface that is concave outward in the radial direction. The second inclined surface 133a is curved surface that is concave outward in the radial direction. In the same manner as the above embodiment, the first inclined surface 132a and the second inclined surface 133a reduce the vibration of the fan case 131 produced by the vibration of the motor 60 in accordance with the angle of line tangential to the sealing member 70. In FIG. 8B, the first inclined surface 132a and the second inclined surface 133a of the fan case 131 are curved surfaces. However, either one may be a tapered surface. Further, at least one of the third inclined surface 63a and the fourth inclined surface 63b of the motor 60 may be a concavely curved surface.

The shape of the seal fastener 50 and the case body 30 and the location and means for joining the seal fastener 50 with the case body 30 may be changed in any manner. For example, as shown in FIGS. 9A and 9B, a seal fastener 143 does not have to be flat and may be configured so that a case body 142 of a fan case 141 surrounds an outer circumferential surface 143a of the seal fastener 143.

Figure 9A:
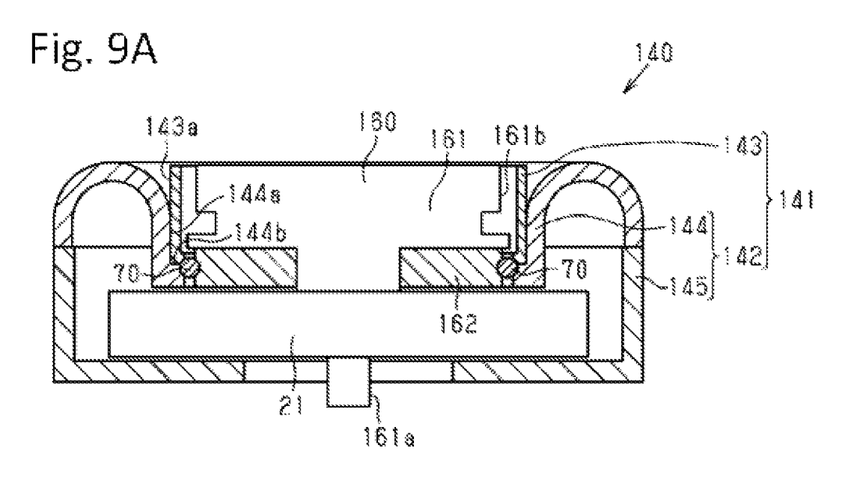
FIG. 9A is a schematic cross-sectional diagram showing another modified example of the blowing device.
Figure 9B:
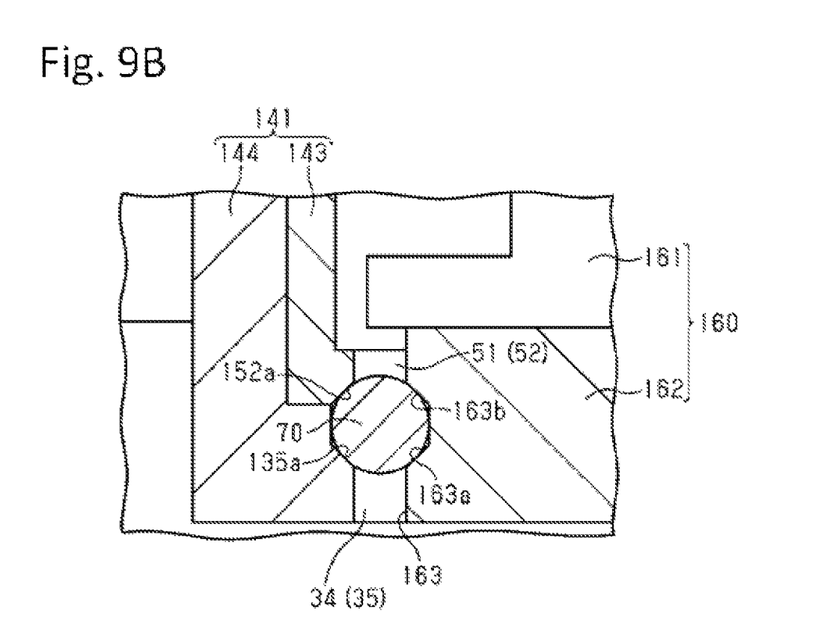
FIG. 9B is a partially enlarged cross-sectional diagram of FIG. 9A.

A blowing unit 140 of the modified example shown in FIG. 9 includes the fan case 141, a motor 160, and the sealing member 70. The fan case 141 includes the case body 142, which accommodates the fan 21, and the seal fastener 143, which is fixed to the case body 142. The motor 160 includes a rotation shaft 161a, a motor body 161, and a seal holding member 162. The rotation shaft 161a includes a distal end portion that projects from the motor body 161 and is joined with the fan 21. Portions of the rotation shaft 161a excluding the distal end portion may be covered by the motor body 161. The seal holding member 162 is configured to support the motor body 161 in the fan case 141 in cooperation with the sealing member 70.

The seal fastener 143 is arranged to surround at least part of the motor body 161 of the motor 160 and at least part of the seal holding member 162. The seal fastener 143 is, for example, shaped to be cylindrical.

The case body 142 is arranged to surround the outer circumferential surface 143a of the seal fastener 143. The case body 142 may include a first case 144 and a second case 145. For example, the first case 144 may be configured as a ring-shaped cap joined with the second case 145. The first case 144 may include an inner circumferential surface 144a that surrounds the outer circumferential surface 143a of the seal fastener 143. The first case 144 may include a step or an inwardly-directed flange 144b to support the seal fastener 143, for example, from below.

The case body 142 is configured so that a cylindrical groove or a cylindrical space is defined between the inner circumferential surface 144a of the first case 144, which is the inner circumferential surface of the case body 142, and an outer circumferential surface 161b of the motor body 161 for insertion of the seal fastener 143.

The seal fastener 143 may be fixed to the first case 144 by planar contact or engagement of the inner circumferential surface 144a of the first case 144 with the outer circumferential surface 143a of the seal fastener 143. The first case 144 may be joined with the seal fastener 143 in a detachable manner, for example, through a Bayonet-type connection. The first case 144 may be fixed to the seal fastener 143 by a screw (not shown). The first case 144 may be joined with the seal fastener 143 through any joining means.

The second case 145 may be configured to be joined with the first case 144 and may be configured in the same manner as, for example, the second case 41 of the embodiment.

As shown in FIG. 9B, the first case 144 includes the inner circumferential surface 35 that defines the opening 34, which serves as part of a motor insertion port. The seal fastener 143 includes the inner circumferential surface 52 that defines the opening 51, which serves as another part of the motor insertion port. The opening 51 of the seal fastener 143 is coaxially connected with the opening 34 of the first case 144 and forms the motor insertion port.

The inner circumferential surface 35 of the first case 144 includes a first inclined surface 135a. The inner circumferential surface 52 of the seal fastener 143 includes a second inclined surface 152a. The seal holding member 162 included in the motor 160 includes an outer circumferential surface 163 that is surrounded by the first inclined surface 135a of the first case 144 and the second inclined surface 152a of the seal fastener 143. The outer circumferential surface 163 includes a third inclined surface 163a and a fourth inclined surface 163b, which define an annular space for receiving the sealing member 70 in cooperation with the first inclined surface 135a and the second inclined surface 152a. The first inclined surface 135a, second inclined surface 152a, third inclined surface 163a, and fourth inclined surface 163b may be configured in the same manner as the above embodiment or modified examples.

The modified example shown in FIG. 9 has the following advantages in addition to the advantages of above-described embodiment and modified examples.

The fan case 141 is configured to surround the motor body 161 of the motor 160 so that the cylindrical seal fastener 143 can be arranged upright between the inner circumferential surface 144a of the fan case 141 and the outer circumferential surface 161b of the motor body 161. This layout reduces the footprint of the seal fastener 143 and is advantageous for reducing the size of the blowing unit 140. The shape and/or position of the seal fastener 143 improves the rigidity of the seal fastener 143 in the axial direction of the motor 160. This reduces the amplitude of the vibration of the fan case 141 r produced by axial vibration transmitted from the motor 160. Thus, the noise is reduced.

The seal fastener 143 is joined with or connected to the inner circumferential surface 144a of the fan case 141 at a radially outer side of the outer circumferential surface 161b of the motor body 161. The seal fastener 143 and the fan case 141 can surround most of, and preferably, all of, the outer circumferential surface 161b of the motor 160 in the axial direction (also referred to as height direction) of the motor 160. This layout is advantageous for protecting the motor 160.

The invention claimed is:

1. A blowing device, comprising:
a fan;
a motor that includes a rotation shaft to which the fan is coupled, wherein the rotation shaft defines an axial direction and radial direction of the blowing device;
a fan case that accommodates the fan and includes a motor insertion port into which the motor is inserted; and
an elastic and annular sealing member located between the motor insertion port and the motor, wherein
the fan case includes an inlet for drawing gas into the fan case as the fan rotates, and a discharge portion configured to discharge gas out of the fan case as the fan rotates,
an inner circumferential surface of the motor insertion port includes a first inclined surface and a second inclined surface that is located at an axially-outer region of the fan case than the first inclined surface, wherein the first inclined surface has an inner diameter that is smaller at a side of the first inclined surface farther from the second inclined surface than a side of the first inclined surface closer to the second inclined surface, and the second inclined surface has an inner diameter that is smaller at a side of the second inclined surface farther from the first inclined surface than a side of the second inclined surface closer to the first inclined surface,
the motor includes an outer circumferential surface opposed to the inner circumferential surface of the motor insertion port, the outer circumferential surface having a third inclined surface and a fourth inclined surface that is located at an axially-outer region of the fan case than the third inclined surface, wherein the third inclined surface has an outer diameter that is larger at a side of the third inclined surface farther from the fourth inclined surface than a side of the third inclined surface closer to the fourth inclined surface, and the fourth inclined surface has an outer diameter that is larger at a side of the fourth inclined surface farther from the third inclined surface than a side of the fourth inclined surface closer to the third inclined surface, and
the sealing member contacts at least one of the first inclined surface and the second inclined surface and at least one of the third inclined surface and the fourth inclined surface.

2. The blowing device according to claim 1, wherein the motor includes a motor body, which drives the fan, and a motor-side fastener, which includes the outer circumferential surface and to which the motor body is fixed.

3. The blowing device according to claim 2, wherein the motor-side fastener includes:
a first fastener, which includes the third inclined surface, and a second fastener, which includes the fourth inclined surface.

4. The blowing device according to claim 3 further comprising a viscous member located between the first fastener and the second fastener.

5. The blowing device according to claim 4, wherein the viscous member includes an adhesive sheet or a gel sheet.

6. The blowing device according to claim 1, wherein the fan case includes a case body that defines an accommodation space for accommodating the fan, and a case-side fastener coupled to an upper surface of the case body, wherein the case body includes the first inclined surface, and the case-side fastener includes the second inclined surface.

7. The blowing device according to claim 6, wherein the case body and the case-side fastener are formed from different materials.

8. The blowing device according to claim 6, further comprising a viscous member located between the case body and the case-side fastener.

9. The blowing device according to claim 8, wherein the viscous member includes an adhesive sheet or a gel sheet.

10. The blowing device according to claim 1, wherein:
at least one of the first inclined surface and the second inclined surface are curved to be concave radially outward, and
at least one of the third inclined surface and the fourth inclined surface is curved to be concave radially outward.

11. A fluid control device, comprising the blowing device according to claim 1; and a controller that controls the blowing device.

* * * * *

UNITED STATES PATENT AND TRADEMARK OFFICE
CERTIFICATE OF CORRECTION

PATENT NO. : 11,338,100 B2
APPLICATION NO. : 16/571649
DATED : May 24, 2022
INVENTOR(S) : Yuzo Higashiyama It is certified that error appears in the above-identified patent and that said Letters Patent is hereby corrected as shown below:

On the Title Page (63); Related U.S. Application Data:
"Continuation of application PCT/JP2019/009415" should be --Continuation of application PCT/JP2018/009415--

Signed and Sealed this
Eighteenth Day of April, 2023

Katherine Kelly Vidal
*Director of the United States Patent and Trademark Office*